US00PP31020P3

(12) United States Plant Patent
Wain

(10) Patent No.: US PP31,020 P3
(45) Date of Patent: Nov. 5, 2019

(54) ***CHRYSANTHEMUM* PLANT NAMED 'DOCHRYSPUR'**

(50) Latin Name: ***Chrysanthemum* X *morifolium***
Varietal Denomination: Dochryspur

(71) Applicant: DUMMEN GROUP B.V., De Lier (NL)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,277

(22) Filed: Feb. 16, 2018

(65) Prior Publication Data

US 2019/0261545 P1 Aug. 22, 2019

(51) Int. Cl.
*A01H 5/02* (2018.01)
*A01H 6/14* (2018.01)

(52) U.S. Cl.
USPC ..... Plt./286

(58) Field of Classification Search
USPC ..... Plt./286
See application file for complete search history.

(56) References Cited

PUBLICATIONS www.dummenorange.com/app/externalresource/site/documents/7/07+Pot+Plants+v07.pdf (4 pages total). (Year: 2017).*

* cited by examiner

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'Dochryspur', characterized by its upright to outwardly spreading and uniformly mounded plant habit; medium in height and moderately vigorous growth habit; freely branching habit; dense and full plant form; uniform and freely flowering habit; large decorative-type inflorescences with dark red purple-colored ray florets; and when grown under controlled daylength/nyctoperiods, flowering response time is about 50 days.

1 Drawing Sheet

Botanical designation: *Chrysanthemum* X *morifolium*.
Cultivar denomination: 'DOCHRYSPUR'.

BACKGROUND OF THE INVENTION

The present invention relates to a new and distinct *Chrysanthemum* plant, botanically known as *Chrysanthemum* X *morifolium*, commercially grown as a potted *Chrysanthemum* plant and hereinafter referred to by the name 'Dochryspur'.

The new *Chrysanthemum* plant is a product of a planned breeding program conducted by the Inventor in Fareham, Hampshire, United Kingdom. The objective of the breeding program is to create new potted *Chrysanthemum* plants with numerous attractive inflorescences.

The new *Chrysanthemum* plant originated from a cross-pollination made in January, 2014 by the Inventor in Fareham, Hampshire, United Kingdom of a proprietary selection of *Chrysanthemum* X *morifolium* identified as code number 807686, not patented, as the female, or seed, parent with a proprietary selection of *Chrysanthemum* X *morifolium* identified as code number 807678, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2014.

Asexual reproduction of the new *Chrysanthemum* plant by terminal vegetative cuttings was first conducted in Fareham, Hampshire, United Kingdom in December, 2014. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dochryspur'. These characteristics in combination distinguish 'Dochryspur' as a new and distinct *Chrysanthemum* plant:

1. Upright to outwardly spreading and uniformly mounded plant habit.
2. Medium in height and moderately vigorous growth habit.
3. Freely branching habit; dense and full plant form.
4. Uniform and freely flowering habit.
5. Large decorative-type inflorescences with dark red purple-colored ray florets.
6. Grown under controlled daylength/nyctoperiods, flowering response time is about 50 days.

Plants of the new *Chrysanthemum* can be compared to plants of the female parent selection. Plants of the new *Chrysanthemum* differ primarily from plants of the female parent selection in ray floret color as of the female parent selection have bronze-colored ray florets.

Plants of the new *Chrysanthemum* can be compared to plants of the male parent selection. Plants of the new *Chrysanthemum* differ primarily from plants of the male parent selection in time to flower as plants of the male parent selection flower about two days earlier.

Plants of the new *Chrysanthemum* can be compared to plants of *Chrysanthemum* X *morifolium* 'Chrystal Aubergine', not patented. In side-by-side comparisons, plants of the new *Chrysanthemum* differ primarily from plants of 'Chrystal Aubergine' in time to flower as plants of the new *Chrysanthemum* flower about four days later than plants of 'Chrystal Aubergine'. In addition, plants of the new *Chrysanthemum* are taller than plants of 'Chrystal Aubergine'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a top perspective view of a typical flowering plant of 'Dochryspur' grown in a container.

DETAILED BOTANICAL DESCRIPTION

The aforementioned photograph and following observations and measurements describe plants grown during the winter in 14-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were propagated under long day/short night conditions for two weeks and then grown under short day/long night conditions to induce inflorescence initiation and development. Plants were nine weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum* X *morifolium* 'Dochryspur'.

Parentage:

- *Female, or seed, parent.*—Proprietary selection of *Chrysanthemum* X *morifolium* identified as code number 807686, not patented.
- *Male, or pollen, parent.*—Proprietary selection of *Chrysanthemum* X *morifolium* identified as code number 807678, not patented.

Propagation:

- *Type.*—Terminal vegetative cuttings.
- *Time to initiate roots, summer.*—About ten days at temperatures about 21° C.
- *Time to initiate roots, winter.*—About twelve days at temperatures about 21° C.
- *Time to produce a rooted young plant, summer.*—About three weeks at temperatures about 21° C.
- *Time to produce a rooted young plant, winter.*—About four weeks at temperatures about 21° C.
- *Root description.*—Medium in thickness, fleshy; typically light brown in color, actual color of the roots is dependent on substrate composition, water quality, fertilizer type and formulation, substrate temperature and physiological age of roots.
- *Rooting habit.*—Freely branching; dense.

Plant description:

- *Plant and growth habit.*—Herbaceous decorative-type potted *Chrysanthemum*; stems upright to outwardly spreading giving a uniformly mounded appearance to the plant; numerous lateral branches and relatively short internodes, dense and full plant form; moderately vigorous growth habit; moderate growth rate; typically grown as a spray-type.
- *Plant height.*—About 17 cm.
- *Plant width.*—About 22 cm.
- *Branching habit.*—Freely branching habit; about four lateral branches develop after removal of terminal apex (pinching).
- *Lateral branches.*—Length: About 6 cm. Diameter: About 2 mm. Internode length: About 3 cm. Strength: Strong. Aspect: About 40° from vertical and bending upwardly. Texture: Fine pubescence. Color: Close to 138A.

Leaf description:

- *Arrangement.*—Alternate, simple.
- *Length.*—About 8 cm.
- *Width.*—About 4 cm.
- *Shape.*—Palmately-lobed; roughly ovate with three to five lobes.
- *Apex.*—Cuspidate.
- *Base.*—Attenuate.
- *Margin.*—Slightly dentate and palmately lobed; sinuses between lateral lobes mostly divergent.
- *Texture, upper and lower surfaces.*—Fine pubescence; slightly rough; veins prominent on lower surface.
- *Color.*—Developing leaves, upper surface: Close to 137A. Developing leaves, lower surface: Close to 137C. Fully expanded leaves, upper surface: Close to N137A; venation, close to 147C. Fully expanded leaves, lower surface: Close to 147B; venation, close to 147D.
- *Petioles.*—Length: About 2 cm. Diameter: About 2 mm. Texture, upper and lower surfaces: Fine pubescence; slightly rough. Color, upper surface: Close to 147C. Color, lower surface: Close to 147D.

Inflorescence description:

- *Form and flowering habit.*—Decorative-type inflorescence form with ligulate-shaped ray florets; inflorescences borne on terminals above and beyond the foliar plane; disc and ray florets arranged acropetally on a capitulum; freely flowering habit with about 15 fully opened inflorescences at one time.
- *Fragrance.*—Mildly fragrant; pungent, herbaceous.
- *Flowering response.*—Grown under controlled short day/long night conditions, response time is about 50 days.
- *Inflorescence longevity.*—Inflorescences maintain good color and substance for about two to three weeks on the plant; inflorescences persistent.
- *Inflorescence buds.*—Height: About 3 mm. Diameter: About 5 mm. Shape: Oblate. Color: Close to 137A.
- *Inflorescence diameter.*—About 7 cm.
- *Inflorescence height.*—About 2 cm.

*Receptacles*.—Height: About 3 mm. Diameter: About 3 mm. Shape: Conical. Color: Close to 145B.

*Ray florets*.—Number of ray florets per inflorescence: About 145 ray florets arranged in about seven whorls. Orientation: Initially upright, then about 80° from vertical. Length: About 4 cm. Width: About 7 mm. Shape: Ligulate; double-keeled and slightly concave. Apex: Rounded. Base: Fused into a short tube. Margin: Entire. Texture, upper and lower surfaces: Smooth, glabrous. Color: When opening, upper surface: Close to 59A. When opening, lower surface: Close to N79C. Fully opened, upper surface: Close to 59B; with development, color becoming closer to N77B. Fully opened, lower surface: Close to N79C; with development, color becoming closer to 77B.

*Disc florets*.—Disc floret development has not been observed on plants of the new *Chrysanthemum* to date.

*Phyllaries*.—Number of phyllaries per inflorescence: About 18 arranged in about three whorls. Length: About 9 mm. Width: About 3 mm. Shape: Lanceolate. Apex: Acute. Base: Obtuse. Margin: Entire. Texture, upper surface: Smooth, glabrous; waxy. Texture, lower surface: Fine pubescence; waxy. Color, upper surface: Close to 143C. Color, lower surface: Close to 143A.

*Peduncles*.—Length, terminal peduncle: About 2.5 cm. Diameter, terminal peduncle: About 2 mm. Angle: Erect to about 15° from vertical. Strength: Moderately strong, flexible. Texture: Densely pubescent. Color: Close to 138B.

*Reproductive organs*.—Androecium: None observed. Gynoecium: Present only on ray florets. Pistil length: About 5 mm. Stigma shape: Bi-parted. Stigma color: Close to 5A. Style length: About 3 mm. Style color: Close to 145B. Ovary color: Close to 1C.

*Seeds and fruits*.—Seed and fruit production has not been observed on plants of the new *Chrysanthemum* to date.

Disease & pest resistance: Resistance to pathogens and pests common to *Chrysanthemum* plants has not been observed on plants of the new *Chrysanthemum* to date.

Temperature tolerance: Plants of the new *Chrysanthemum* have been observed to tolerate temperatures from about 0° C. to about 35° C.

It is claimed:

1. A new and distinct *Chrysanthemum* plant named 'Dochryspur' as illustrated and described.

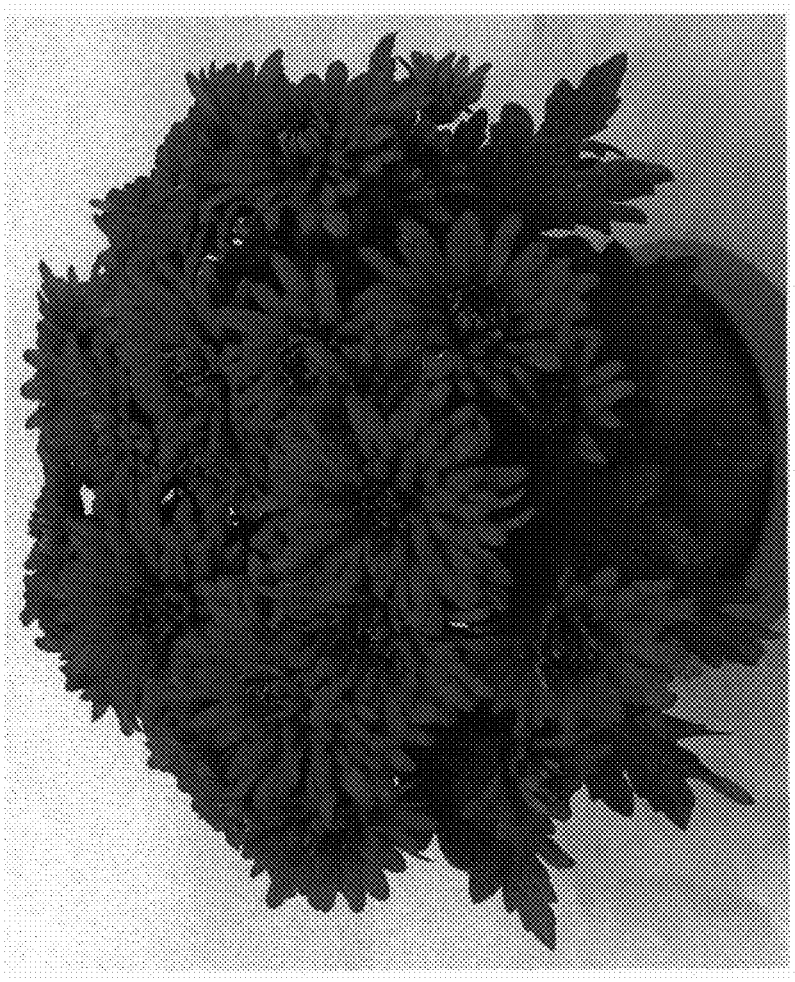

* * * * *